US005630823A

United States Patent [19]
Schmitz-Rode et al.

[11] Patent Number: 5,630,823
[45] Date of Patent: May 20, 1997

[54] APPARATUS FOR FRAGMENTATION OF A LUNG OR HEART EMBOLUS

[75] Inventors: Thomas Schmitz-Rode; Rolf W. Günther, both of Aachen, Germany

[73] Assignee: William Cook Europe A/S, Bjaeverskov, Denmark

[21] Appl. No.: 459,272

[22] Filed: Jun. 2, 1995

[30] Foreign Application Priority Data

Jun. 17, 1994 [DE] Germany ............... 9409863 U

[51] Int. Cl.$^6$ ............................................. A61B 17/22
[52] U.S. Cl. .................. 606/128; 606/159; 604/281; 604/164
[58] Field of Search ...................... 606/128, 127, 606/108, 159, 106; 604/280, 281, 164, 95; 128/772

[56] References Cited

U.S. PATENT DOCUMENTS

| | | | |
|---|---|---|---|
| 1,207,479 | 12/1916 | Bisgaard | 604/95 |
| 4,405,314 | 9/1983 | Cope | 604/281 |
| 4,740,195 | 4/1988 | Lanciano | 604/95 |
| 4,747,840 | 5/1988 | Ladika et al. | 604/281 |
| 5,037,403 | 8/1991 | Garcia | 604/281 |
| 5,312,357 | 5/1994 | Buijs et al. | 604/164 |
| 5,330,484 | 7/1994 | Güther et al. | |
| 5,352,198 | 10/1994 | Goldenberg et al. | 604/95 |

FOREIGN PATENT DOCUMENTS 0549458  6/1993  European Pat. Off. .

OTHER PUBLICATIONS

Cook®, "Diagnostic and Interventional Products for Radiology, Cardiology and Surgery: Aortography, Ventriculography, and Multipurpose Catheters," William Cook Europe, 1987, p. 10.

Primary Examiner—Robert A. Hafer
Assistant Examiner—Benjamin Koo
Attorney, Agent, or Firm—Richard J. Godlewski

[57] ABSTRACT

Method and apparatus for fragmentation of a lung embolus. The apparatus includes a catheter that is introduced over a guide wire to the site of the lung embolism in the vascular system of a patient. When the guide wire is withdrawn from the distal end segment of the catheter, the distal end segment bends back proximally. An opening in the bend of the catheter is in line with the central axis of the catheter when the distal end segment is in a curved configuration. The guide wire is then advanced to extend distally from the catheter opening past the embolism and stabilize the longitudinal position of the catheter in the blood vessel. The apparatus also includes a thread for pulling the bent distal end segment into a generally oval-shaped loop condition and stabilizing the loop about the embolism. The looped catheter is then rotated and moved longitudinally back and forth for mechanically destroying the embolism. To return the catheter to a straight condition, the rigid guide wire is withdrawn from the catheter, and a guide wire with a resilient J-tip is advanced to the distal end segment of the catheter. The J-tip guide wire follows the catheter past the catheter opening, thereby straightening the catheter for removal from the body. The apparatus optionally includes a handle or motor positioned at the proximal end of the apparatus.

14 Claims, 4 Drawing Sheets

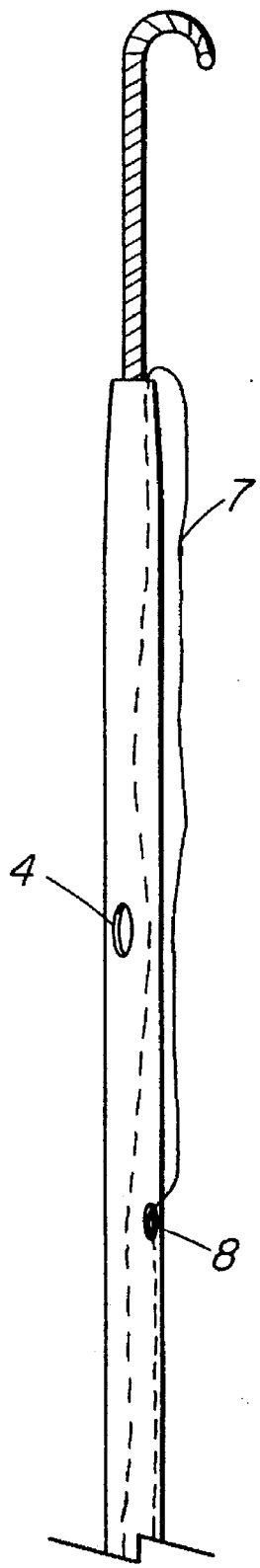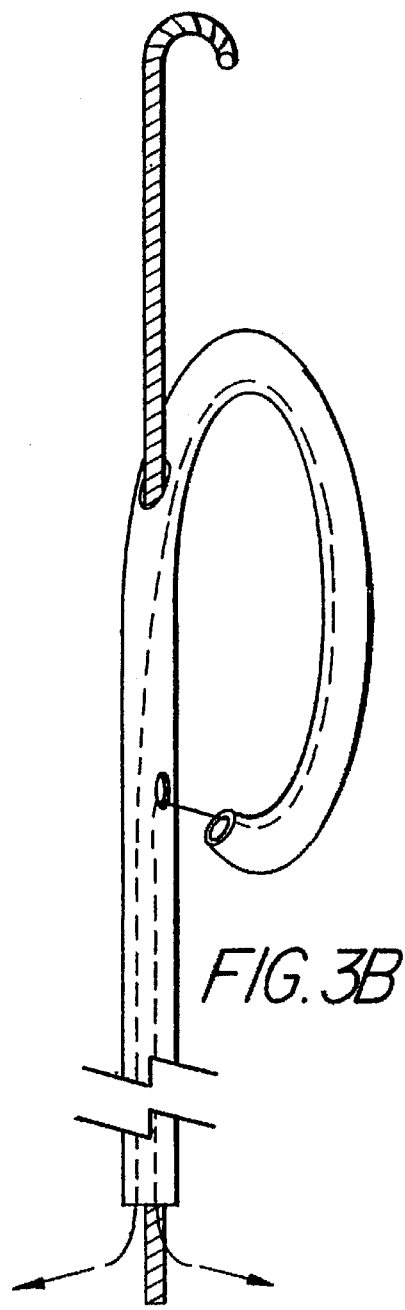
FIG. 3A
FIG. 3B

APPARATUS FOR FRAGMENTATION OF A LUNG OR HEART EMBOLUS

TECHNICAL FIELD

This invention relates generally to medical devices and, in particular, to an apparatus and a method of use for fragmenting a lung embolus.

BACKGROUND OF THE INVENTION

In industrial countries, the third most frequent cause of death is lung emboli. Ten percent of patients with acute lung emboli die from heart failure. Dissolution by medicine of the embolus (thrombolysis) takes hours. The patient often dies before a hemodynamic improvement occurs. Operational removal of the embolus in accordance with the so-called Tendelenburg operation entails a comparatively high rate of mortality.

With a combined treatment comprising mechanical destruction of lung emboli and a subsequent selective thrombolysis of the resulting fragments, it has in some cases been possible to obtain promising treatment results. In this case, the fragmentation of an embolus took place by manipulation with diagnostic standard pulmonary catheters. Such a catheter is advanced by means of a guide wire past an embolus towards the periphery. After the withdrawal of the guide wire, the catheter assumes a curved configuration, for instance, in the form of a pig tail. Withdrawal of the catheter then cuts the embolus into pieces. This process must be repeated several times and results in a relatively rough fragmentation of the embolus. By this maneuver, a lowering of the pulmonary arterial pressure was attained, and consequently the risk of heart attack and subsequent death was reduced.

This described technique for the fragmentation of pulmonary emboli is fairly complicated and protracted. Furthermore, this technique is very rough, as the pig tail catheters are not intended for fragmentation of a lung embolus.

One apparatus for the treatment of lung emboli known as a "Thrombolyseur" includes a rotating basket that is unfolded by centrifugal force for fragmentation of the embolic material. Thrombotic material in the blood flow path towards the lung is caught by the created whirl and mechanically fragmented. A problem with the Thrombolyseur is that contact between the basket treads and the arterial wall cannot be avoided and can lead to injury.

Another apparatus for the treatment of lung emboli is known as an "Impeller-Katheter" in which a rotor (impeller) is positioned in the center of a self-expanding, stationary protective basket.

A problem with both of these apparatuses is that each rotational body is driven through a flexible shaft positioned in the interior of a catheter by an external drive at 100,000 to 150,000 rpm. The high rotational speed results in high load on the material and makes these apparatuses prone to defects. Due to the complexity of both apparatuses, the risk of erroneous handling by an inadequately trained operator is significant.

SUMMARY OF THE INVENTION

The object of the present invention is to provide an apparatus for fragmentation of a lung embolus, which apparatus has a simple construction, is easy to handle, and allows an effective and atraumatic fragmentation treatment of an embolus.

To meet this object, the apparatus preferably comprises a torsionally stiff or stable catheter and a wire guide extendable therethrough. The distal end segment of the catheter has a bend which is controllable with the wire guide. The bend has an opening advantageously positioned on the outer side of the catheter which is in line with the central axis of the catheter.

The torsionally stiff or stable catheter is simple and can quickly by means of the guide wire be placed in the pulmonary artery. During introduction of the apparatus to the area of the embolus, the guide wire extends over the whole length of the catheter and prevents the distal catheter end segment from assuming a curved configuration until the guide wire is withdrawn therefrom. By a renewed advancing, the distal end of the guide wire comes out of an opening in a bend of the curved catheter, which opening is aligned with the central axis of the catheter. The guide wire serves as rotational axis for the torsionally stable catheter. After anchoring the guide wire distally or peripherally in the lung artery system, the catheter is rotated by a handle or by a mechanical drive such as an electric motor positioned at the proximal end of the catheter. By rotation of the curved or looped distal catheter end segment within the embolic blockage, the embolic material can be fragmented. The fragmentation of the embolic material is also provided by moving the catheter longitudinally back and forth over the stationary guide wire. As a result, the thrombic material is broken into pieces by the curved or looped distal catheter end segment passing by the embolus. Advantageously, the uncomplicated catheter tip design is atraumatic to vessel walls.

According to a preferred embodiment of the apparatus according to the invention, a free end of the catheter bend points toward the central axis of the catheter, whereby the bend is formed into an oval loop. The small diameter of the loop is preferably 7 to 10 mm, and the big diameter of the loop is preferably two to three times larger than the small diameter.

In order to use the apparatus according to the invention for diagnosing a lung embolus, additional openings are arranged in the distal end segment of the catheter. The cross section of the openings is smaller than the cross section of the guide wire. The lateral injection openings are positioned transversely to the axis of the guide wire so that the guide wire is prevented from unintentionally penetrating through one of these openings and impeding proper handling and positioning of the catheter. Through the lateral openings, a thrombolytic agent can be injected during the fragmentation process or in connection therewith, which supports the dissolution of the thrombus medicinally.

When the guide wire is positioned, a so-called Y-rotation adaptor is connected therewith at the proximal catheter end. The adaptor does not impede the rotation of the catheter and further seals the guide wire with respect to the proximal end of the catheter. The adaptor allows injection of a thrombolytic agent or contrast agent through the lateral openings.

According to another embodiment of the invention, a thread, one end of which protrudes from the proximal end of the catheter, passes through the catheter, exits the distal end of the catheter, is introduced again in the catheter through an opening, and protrudes likewise with its other end from the proximal end of the catheter. By this embodiment, the loop formed from the curved or bent distal catheter end segment can be stabilized by means of tightening the two proximal thread ends, which improves the cutting effect of the curved or bent segment on an embolus.

BRIEF DESCRIPTION OF THE DRAWING

In the drawing embodiments of the apparatus according to the invention is shown schematically and will be explained in further detail in the following. In the drawing;

FIG. 3A depicts the apparatus according to FIGS. 1A–C with a thread running through the catheter lumen when the catheter is straightened by the guide wire;

FIG. 3B depicts the apparatus according to FIGS. 1A–C with a thread running through the catheter lumen after withdrawal and renewed advancing of the guide wire and tightening of the thread.

DETAILED DESCRIPTION

Figure 1A:
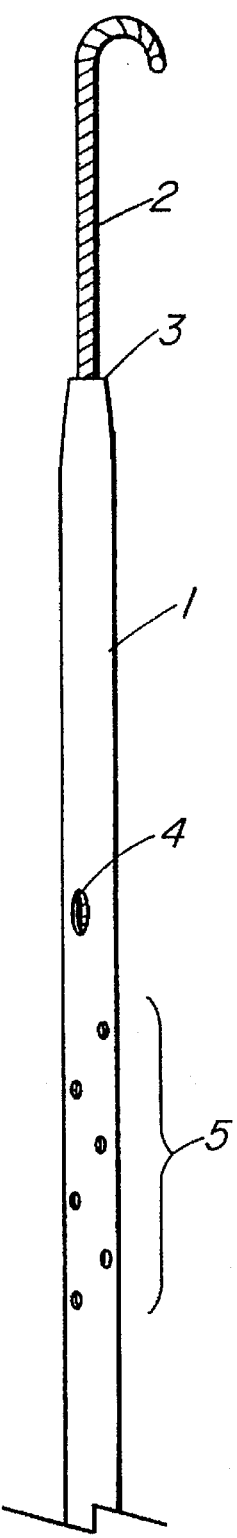
FIG. 1A depicts the distal end segment of the catheter in an unbent or straightened condition with a guide wire protruding from its end.
Figure 2A:
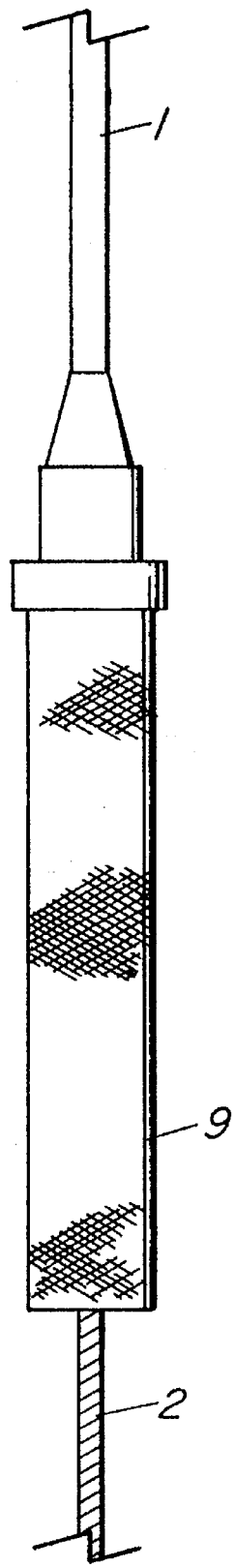
FIG. 2A depicts the proximal end of the apparatus with a handle threaded onto the catheter.
Figure 2B:
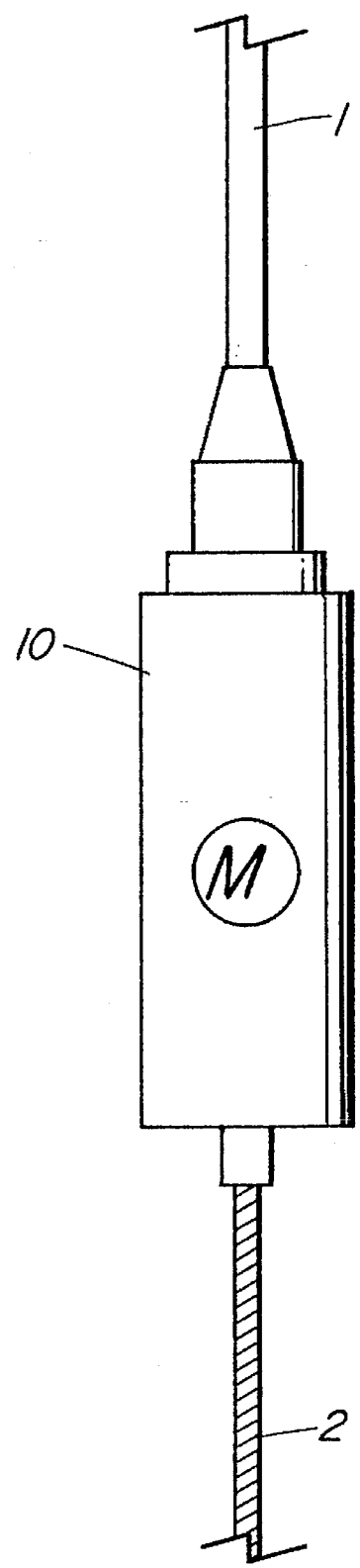
FIG. 2B depicts the proximal end of the apparatus with an electric motor connected to the catheter.

The apparatus depicted in FIG. 1A comprises a torsionally stiff or stable catheter 1 and a guide wire 2, which forms the rotational axis of the catheter 1. As depicted in FIGS. 2A and 2B, the proximal end of the catheter is provided with a handle 9 or a motor 10, respectively.

Figure 1B:
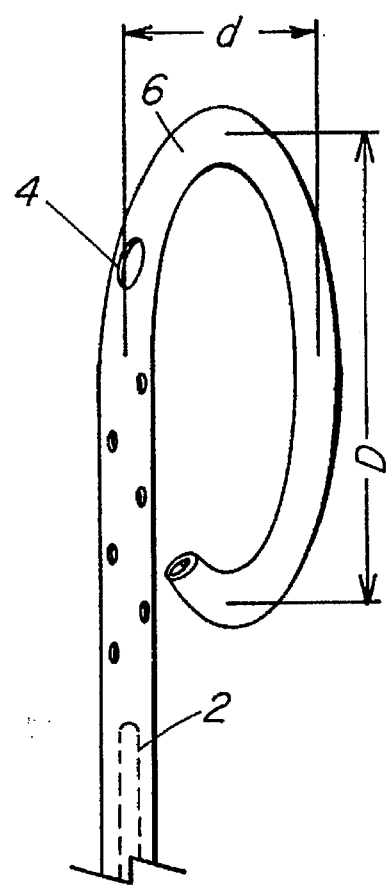
FIG. 1B depicts the catheter according to FIG. 1A, but with the guide wire withdrawn.

During introduction into the arterial system and the right heart atrium, the catheter 1 is positioned in the straightened condition on the guide wire 2, as depicted in FIG. 1A. The guide wire protrudes from the distal end 3 of the catheter 1. When the guide wire is withdrawn, the distal end segment of the catheter 1 assumes a preformed bend by elastic restoring forces into a curved configuration or loop 6 as depicted in FIG. 1B. This curved configuration or loop is preferably oval, the small diameter d being 10 mm and the big diameter D being two or three times as big as d.

In this curved configuration, the right side of the heart and the pulmonary artery can be examined conveniently and atraumatically. After positioning the catheter loop 6 in the lung flow path, an angiography can be carried out. Contrast agent comes out of lateral openings 5 for angiography of the artery lumen.

Figure 1C:
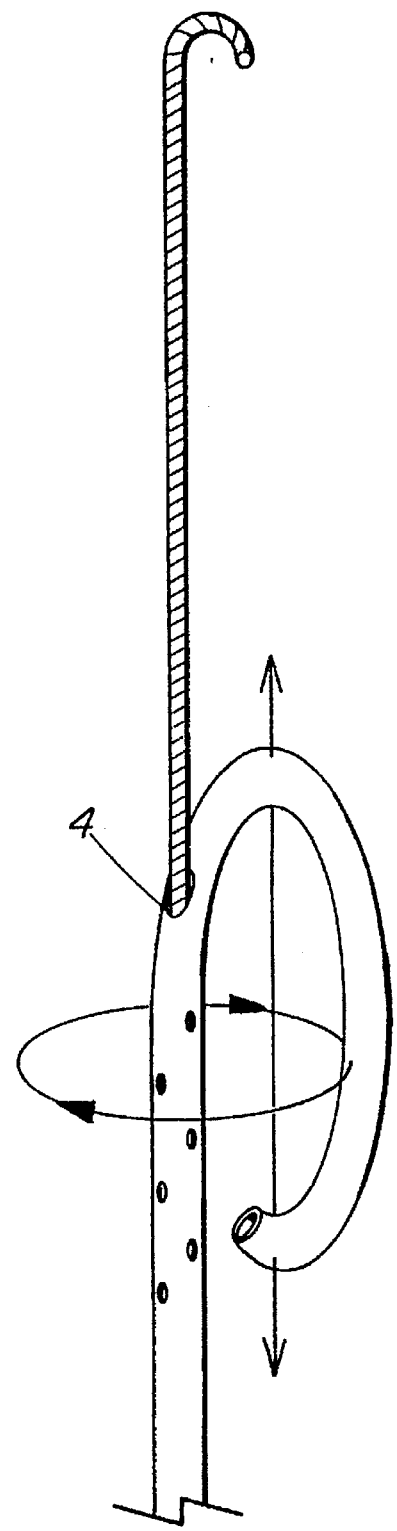
FIG. 1C depicts the catheter according to FIG. 1B, but after the guide wire has been advanced through a side opening in the catheter.

After location of the embolus, the guide wire 2 is pushed through the catheter 1 and leaves the interior of the looped catheter through an opening 4 positioned in line with the central axis of the catheter 1, as shown in FIG. 1C. The use of a guide wire with a stiff or rigid distal end permits the guide wire 2 to exit the opening 4 of the catheter. The catheter loop 6 hereby retains its shape against the resistance of the guide wire. The guide wire 2 is advanced past the embolus for stabilizing the position of the catheter 1 in the artery. The looped catheter is then rotated by handle 9 or electric motor 10 at the proximal end of catheter 1. During rotation of the catheter, guide wire 2 serves as a stationary rotational axis. The embolus is fragmented by loop 6 due to the torsional stability of the catheter, which transfers the rotation exerted thereon to the loop 6.

The guide wire 2 can alternatively include a movable core and a J-tip so that the catheter can be straightened by renewed advancing of the guide wire 2. As the resilient, narrowly bent distal end segment of the guide wire 2 is advanced through the catheter, the guide wire follows the course of the central axis of the catheter. Straightening the catheter is used for repositioning the catheter with respect to the embolism or for a further peripheral examination in addition to removal of the catheter from the body of the patient.

During or after embolus fragmentation, a thrombolytic agent can be introduced directly in the embolus through the relatively small, lateral openings 5 or can be injected in the flow area containing the fragments.

As depicted in FIGS. 3A and 3B, a thin, non-stretched thread 7 is passed through the interior of the catheter, exits the distal end of the catheter 1, and returns to the interior of the catheter through an opening 8. The thread 7 returns to the proximal end of the catheter 1. The thread 7 is tightened for stabilizing the catheter loop 6, as depicted in FIG. 3B.

Figures 4A, 4B:
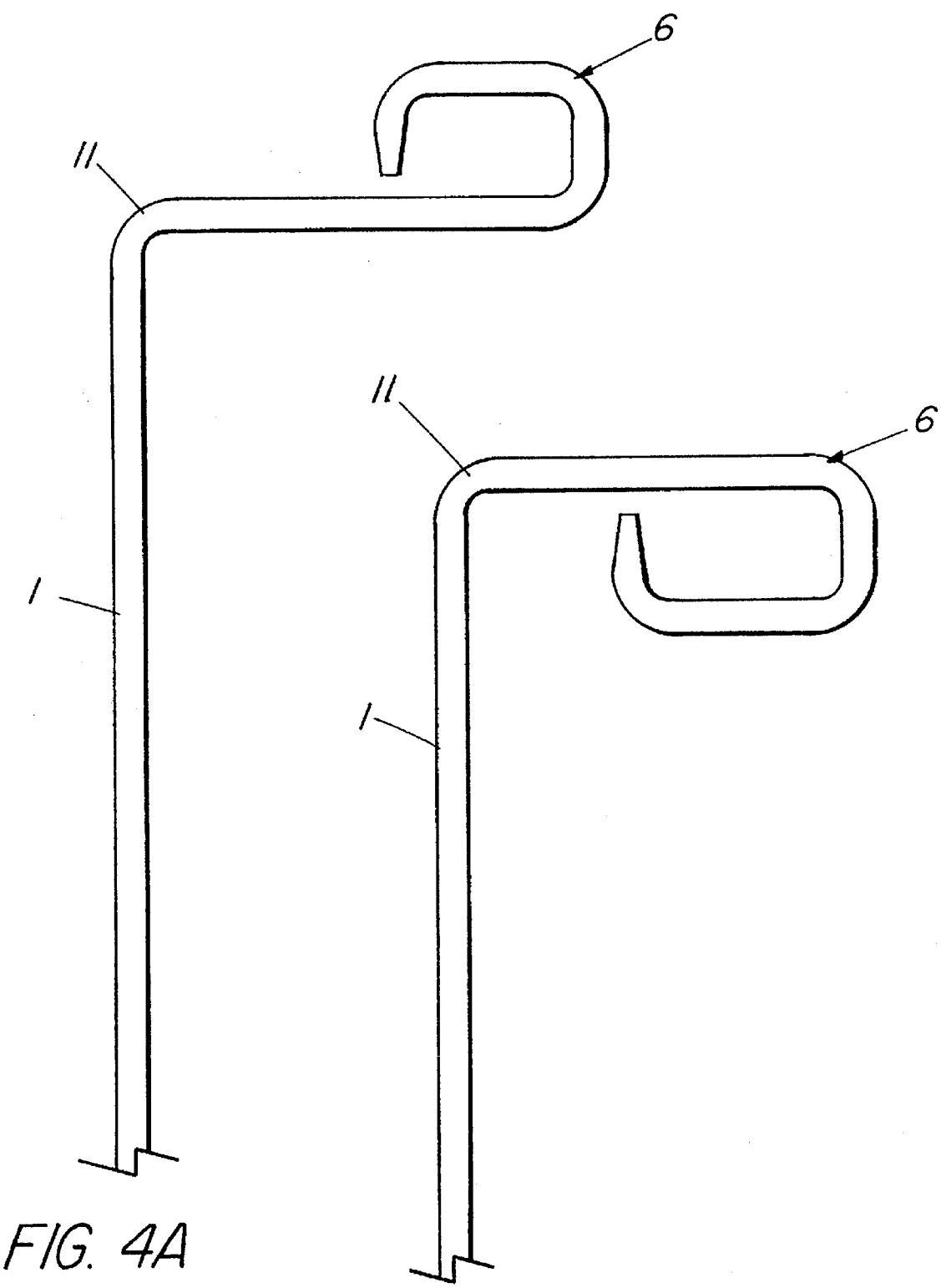
FIGS. 4A and 4B depict angled catheter tips for facilitating examination of the right ventricle of the heart and the pulmonary artery.

A distal end segment 11 of the catheter 1 is angled or bent, as depicted in FIGS. 4A and 4B, for the examination of the right side of the heart and the central lung arteries.

What is claimed is:

1. An apparatus for fragmentation of a lung or heart embolus, comprising:

a torsionally stable catheter (1) having a distal end and a proximal end and a guide wire (2) located within the lumen of the catheter, wherein the distal end of the catheter (1) has a preformed bend (6), said catheter having sufficient rigidity to retain said preformed bend, which is controllable with guide wire (2) wherein an opening is located in the distal end of the catheter (1) in the side of the catheter away from said bend and which is in line with a longitudinal central axis of the catheter (1) in order that the rotation of the catheter will result in the fragmentation of an embolus.

2. An apparatus according to claim 1 wherein a free end of the bend (6) points towards the central axis of the catheter (1) and that the bend forms an oval loop (6).

3. An apparatus according to claim 2 wherein a small diameter (d) of the loop (6) is approximately 7 to 10 mm and a big diameter (D) of the loop (6) is two or three times as big as the small diameter (d).

4. An apparatus according to claim 1 wherein openings (5) are arranged in the distal end segment of the catheter (1), the diameter of said openings being smaller than the cross section of the guide wire (2).

5. An apparatus according to claim 2 wherein openings (5) are arranged in the distal end segment of the catheter (1), the diameter of said openings being smaller than the cross section of the guide wire (2).

6. An apparatus according to claim 3 wherein openings (5) are arranged in the distal end segment of the catheter (1), the diameter of said openings being smaller than the cross section of the guide wire (2).

7. An apparatus according to claim 1 wherein a thread (7), one end of which protrudes from the proximal end of the catheter, is passed through the catheter (1), leaves at the distal end of the catheter (1), is introduced again in the catheter (1) through an opening (8) and protrudes likewise with its other end from the proximal end of the catheter (1).

8. An apparatus according to claim 2 wherein a thread (7), one end of which protrudes from the proximal end of the catheter, is passed through the catheter (1), leaves at the distal end of the catheter (1), is introduced again in the catheter (1) through an opening (8) and protrudes likewise with its other end from the proximal end of the catheter (1).

9. An apparatus according to claim 3 wherein a thread (7), one end of which protrudes from the proximal end of the catheter, is passed through the catheter (1), leaves at the distal end of the catheter (1), is introduced again in the catheter (1) through an opening (8) and protrudes likewise with its other end from the proximal end of the catheter (1).

10. An apparatus according to claim 4 wherein a thread (7), one end of which protrudes from the proximal end of the catheter, is passed through the catheter (1), leaves at the distal end of the catheter (1), is introduced again in the catheter (1) through an opening (8) and protrudes likewise with its other end from the proximal end of the catheter (1).

11. An apparatus according to claim 5 wherein a thread (7), one end of which protrudes from the proximal end of the catheter, is passed through the catheter (1), leaves at the distal end of the catheter (1), is introduced again in the catheter (1) through an opening (8) and protrudes likewise with its other end from the proximal end of the catheter (1).

12. An apparatus according to claim 6 wherein a thread (7), one end of which protrudes from the proximal end of the catheter, is passed through the catheter (1), leaves at the distal end of the catheter (1), is introduced again in the catheter (1) through an opening (8) and protrudes likewise with its other end from the proximal end of the catheter (1).

13. The apparatus of claim 1 further comprising a handle (9) positioned at a proximal end of the catheter.

14. The apparatus of claim 1 further comprising a motor (10) positioned at a proximal end of the catheter.

* * * * *